United States Patent [19]

Popa et al.

[11] Patent Number: 5,082,641

[45] Date of Patent: Jan. 21, 1992

[54] SILICON/TITANIUM OXIDE MFI ZEOLITES

[75] Inventors: Jean-Michel Popa, Drancy; Jean-Luc Guth, Mulhouse; Henri Kessler, Wittenheim, all of France

[73] Assignee: Rhone-Poulenc Chimie, Courbevoie, France

[21] Appl. No.: 197,821

[22] Filed: May 23, 1988

[30] Foreign Application Priority Data

May 22, 1987 [FR] France ................ 87 07187
Mar. 30, 1988 [FR] France ................ 88 04167

[51] Int. Cl.$^5$ .............................................. C01B 33/34
[52] U.S. Cl. .................................. 423/326; 502/64
[58] Field of Search .............. 423/326, 330, 328 T, 423/328 M; 502/85

[56] References Cited

U.S. PATENT DOCUMENTS

| | | | |
|---|---|---|---|
| 4,073,865 | 2/1978 | Flanigen et al. | 423/339 |
| 4,410,501 | 10/1983 | Taramasso et al. | 423/326 |
| 4,478,806 | 10/1984 | Ball et al. | 423/328 T |
| 4,551,321 | 11/1985 | Marusi et al. | 423/328 T |
| 4,596,704 | 6/1986 | Miale et al. | 502/85 |
| 4,666,692 | 5/1987 | Taramasso et al. | 423/326 |
| 4,828,812 | 5/1989 | McCullen et al. | 423/326 |

FOREIGN PATENT DOCUMENTS 0077523  4/1983  European Pat. Off. ........ 423/328 M

Primary Examiner—Michael Lewis
Assistant Examiner—Stuart L. Hendrickson
Attorney, Agent, or Firm—Burns, Doane, Swecker & Mathis

[57] ABSTRACT

Novel MFI zeolites based on the oxides of silicon and titanium, well adapted as selective adsorbents, catalysts and catalyst supports, have the following formula:

$$[Si_{96-x}Ti_x]O_{192}$$

wherein x ranges from about 0.1 to 6.

26 Claims, No Drawings

SILICON/TITANIUM OXIDE MFI ZEOLITES

BACKGROUND OF THE INVENTION

1. Field of the Invention

The present invention relates to novel zeolites based on silica and titanium oxide and to a process for the preparation thereof; more especially this invention relates to the production of MFI zeolites.

2. Description of the Prior Art

Zeolites are crystallized tectosilicates. Their structures consist of conglomerations of TO$_4$ tetrahedrons defining a tridimensional skeleton via the sharing of oxygen atoms. In zeolites of the aluminosilicate type, which are the most common, T represents the tetravalent silicon, together with the trivalent aluminum. The cavities and channels of molecular dimensions of this skeleton accept cations to compensate for the charge deficit related to the presence of the trivalent aluminum in the tetrahedrons. Also known to this art are certain rare zeolites wherein the silicon is replaced by tetravalent germanium. Similarly, trivalent elements, such as gallium and more rarely boron or beryllium, may be substituted for the aluminum.

In general, the composition of the zeolites may be represented by the overall formula: $M_{2/n}O$; $Y_2O_3$; $xZO_2$, in dehydrated and calcined state. Z and Y respectively represent the tetravalent and trivalent elements of the TO$_4$ tetrahedrons; M represents an electropositive element of valence n, such as alkali or alkaline earth metals, and constituting the compensating cations; x may range from 2 theoretically to infinity, in which case the zeolite is a crystallized silica.

Each type of zeolite has a distinct pore structure. The variation in the dimensions and in the form of the pores from one type to another is the reason for the differences in the respective adsorption properties thereof. Only those molecules having certain dimensions and shapes are able to enter the pores of a particular zeolite. In view of these remarkable properties, the zeolites are especially suitable for the purification or separation of gases or liquids, such as, for example, the separation of hydrocarbons by selective adsorption.

The chemical composition, in particular together with the nature of the elements present in the TO$_4$ tetrahedrons and the nature of the exchangeable compensating cations, is also an important factor in the selectivity of adsorption and particularly the catalytic activity of these materials. They are used as catalysts or catalyst supports in the cracking, reforming and modifications of hydrocarbons and in the synthesis of numerous compounds.

Many zeolites exist in nature, i.e., the aluminosilicates, the availability and properties of which do not always satisfy the requirements of industrial applications. Consequently, the research and development effort for novel zeolites essentially of the aluminosilicate type has to date been considerable. Among the numerous examples of such effort, the following references are illustrative: zeolite A (U.S Pat. No. 2,882,243), zeolite X (U.S. Pat. No. 2,882,244), zeolite Y (U.S. Pat. No. 3,130,007), zeolite L (French Patent No. 1,224,154), zeolite T (French Patent No. 1,223,775), zeolite ZSM5 (U.S. Pat. No. 3,702,886), zeolite ZSM12 (U.S. Pat. No. 3,832,444), zeolite ZSM48 (EP 0,015,132).

Zeolites containing titanium in the TO$_4$ tetrahedrons have also been proposed to this art. Compare French Patent No. 2,471,950, EP 104,107 and 100,119 and U.S. Pat. No. 3,329,481. However, the titanium bond in the crystalline system is of the octahedral type, rather than tetrahedral, the substitution of silicon by titanium in the structure of a zeolite being very difficult in the case of the aluminosilicates.

Zeolites are typically obtained from a reaction mixture which is converted in a hydrothermal medium, by a dissolution/recrystallization process, with the crystalline precipitate being calcined after separation and drying to yield an active zeolite.

The reaction mixture contains the elements T to be incorporated into the skeleton of the zeolite; these reagents generally are aqueous gels containing the oxides or hydroxides of the elements T.

The reaction mixture also contains a "mobilizer" promoting the dissolution of these reagents and their transfer from the aqueous phase into the zeolites under formation, and structural agents enabling formation of microporous spaces, together with the stabilization of the zeolite.

Hydroxide ions are used as the mobilizer. Thus, the reaction media generally have a pH higher than 10, on the one hand to insure the dissolution of the sources of silica and the other sources of the elements T, and, on the other, to facilitate the transfer of the soluble species into the zeolite in the process of formation.

Zeolites containing species easily soluble in a basic medium, such as, for example, aluminum, are well synthesized by this method.

However, it appears to be quite difficult to incorporate titanium in the TO$_4$ skeleton of the zeolite, if the reaction medium is basic.

Furthermore, in a basic medium the metastable zeolites are obtained only if the reaction medium is supersaturated with active species. This gives rise to rapid nucleation resulting in small zeolite crystals, without the option of easily controlling the dimensions of such crystals.

In addition, syntheses employing basic reaction mixtures require the use of alkali or alkaline earth metal cations as compensating cations. These cations frequently must be subsequently eliminated, as they affect the catalytic or adsorbent properties of the zeolite. This elimination is typically carried out by repeated ion exchange using NH$_4^+$ cations. The zeolite containing ammonium cations is then calcined to eliminate them in the form of NH$_3$.

SUMMARY OF THE INVENTION

Accordingly, a major object of the present invention is the provision of novel zeolites of the pentasil family which are conspicuously devoid of those disadvantages and drawbacks to date characterizing the state of this art. Such novel zeolites are of the MFI type, based on silica and titanium oxide. These novel MFI zeolites are synthesized from neutral or acid reaction mixtures, enabling, in particular, the incorporation of titanium in the skeleton of the zeolite in large amounts, as well as the production of zeolite crystals having completely controlled dimensions. The novel zeolites according to this invention shall hereinafter be designated as "titanozeosilites".

Briefly, the present invention features novel MFI zeolites, based on silica and titanium oxide, and having, after calcination, the following general formula:

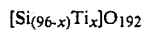

wherein x ranges from about 0.1 to 6.

The MFI zeolites of the invention have a monoclinic crystalline network and the X-ray diffraction pattern set forth in Table I.

In this Table, the extreme values of the different reticular $d_{hkl}$ equidistances are reported and correspond to the limits of concentration of the titanium incorporated in the skeleton of the zeolite, or more precisely the Ti/Si ratio.

Indeed, the identification of the MFI zeolites of the invention may particularly and advantageously be effected by determining their X-ray diffraction spectra.

Such diffraction spectra may be obtained by means of a diffractometer using the conventional powder method entailing the $K\alpha$ radiation of copper. From the position of the diffraction peaks represented by the angle $2\Theta$, the characteristic $d_{hkl}$ reticular equidistances of the sample are calculated by the Bragg equation. The estimate of the error $\Delta$ ($d_{hkl}$) of the measurement of $d_{hkl}$ is calculated, as a function of the absolute measurement error $\Delta$ ($d_{hkl}$) of $d_{hkl}$ applied to the measurement of $2\Theta$, by the Bragg equation. An absolute error ($2\Theta$) equal to $0.2°$ is acknowledged. The relative intensity $I/I^o$ associated with each value of $d_{hkl}$ is estimated from the height of the corresponding diffraction peak. A symbolic scale is frequently used to characterize this intensity: FF=very strong; F=strong; mF=medium to strong; m=medium; mf=medium to weak; f=weak; ff=very weak.

TABLE I

| X-ray diffraction pattern | | | |
|---|---|---|---|
| Extreme values of $d_{hkl}$ (nm) | $I/I_o$ | Extreme values of $d_{hkl}$ (nm) | $I/I_o$ |
| 1.110–1.128 | F-FF | 0.3785–0.3845 | mF |
| 0.991–0.012 | F-FF | 0.3735–0.3795 | m |
| 0.972–0.986 | f | 0.3715–0.3775 | m |
| 0.895–0.906 | ff | 0.3705–0.3765 | m |
| 0.803–0.813 | ff | 0.3645–0.3700 | f |
| 0.741–0.753 | ff broad | 0.3610–0.3670 | f |
| 0.704–0.715 | ff broad | 0.3470–0.3525 | ff |
| 0.666–0.678 | f | 0.3430–0.3485 | f (f) |
| 0.632–0.643 | f | 0.3415–0.3470 | f (f) |
| 0.595–0.605 | mf | 0.3385–0.3439 | ff |
| 0.589–0.598 | f | 0.3341–0.3394 | f (f) |
| 0.568–0.577 | mf | 0.3290–0.3345 | f broad |
| 0.565–0.574 | f shoulder | 0.3240–0.3292 | f |
| 0.555–0.564 | f | 0.3045–0.3099 | f (f) |
| 0.534–0.543 | f (f) | 0.3020–0.3068 | f |
| 0.531–0.539 | f (f) | 0.2978–0.3026 | f |
| 0.510–0.518 | ff | 0.2952–0.2999 | ff shoulder |
| 0.502–0.508 | ff | 0.2944–0.2991 | f |
| 0.496–0.504 | mf | 0.2914–0.2961 | ff |
| 0.485–0.493 | ff | 0.2852–0.2898 | ff broad |
| 0.468–0.476 | ff | 0.2774–0.2818 | ff |
| 0.459–0.466 | f | 0.2722–0.2766 | ff broad |
| 0.444–0.451 | f | 0.2675–0.2720 | ff |
| 0.433–0.441 | f | 0.2606–0.2648 | ff |
| 0.423–0.431 | f | 0.2586–0.2627 | ff |
| 0.4055–0.4125 | ff | 0.2544–0.2585 | ff broad |
| 0.3985–0.4045 | f | 0.2508–0.2548 | ff |
| 0.3835–0.3905 | F | 0.2478–0.2518 | f |
| 0.3805–0.3865 | mF | | |

Also characteristic of the invention, the subject MFI zeolites contain fluorine, with the fluorine concentration advantageously ranging from 0.01 to 0.8% by weight after calcination.

However, the fluorine may be eliminated without modifying the structure of the zeolite according to the invention.

This invention also features a process for the production of the subject MFI zeolites by:

(i) preparing a reaction mixture in an aqueous medium containing at least one source of silicon oxide, a source of titanium oxide, fluoride ions and a structuring agent, the pH of the reaction mixture ranging from about 1.5 to about 10.5;

(ii) crystallizing such reaction medium and recovering the crystalline precipitate therefrom; and (iii) calcining the precipitate at a temperature greater than 450° C.

The X-ray diffraction pattern set forth in Table I is that of a zeolite calcined as above indicated.

DETAILED DESCRIPTION OF THE PREFERRED EMBODIMENTS OF THE INVENTION

More particularly according to the present invention, the use of fluoride ions in the reaction medium, which serve as mobilizing agents, makes it possible to effect the solubilization of the species T (Si and Ti) in a medium having a pH of less than 10. It is thus possible to use $NH_4^+$ ions as the compensating cations, which may be eliminated completely, if so desired, during calcination.

Furthermore, as crystallization takes place in a medium having a pH of less than 10, the rate of nucleation is slower. Thus, it is also possible to produce controlled-size zeolite crystals by regulating the rate of nucleation.

The molar ratios of the different species in the reaction medium range from about 1.5 to about 0.002 for Ti/Si, from about 10 to about 0.004 for F/Si, from about 400 to about 4 for $H_2O$/Si, and for the structuring agent relative to the silicon species, from about 2 to about 0.02.

Advantageously, the Ti/Si molar ratio ranges from 1 to 0.01, F/Si from 6 to 0.06, $H_2O$/Si from 100 to 6 and between the structuring agent and the silicon species, from 1 to 0.04.

Numerous silica sources may be used. Exemplary thereof are silica in the form of hydrogels, aerogels, colloidal suspensions, the silica resulting from precipitation from solutions of soluble silicates or the hydrolysis of silicic esters, such as $Si(OC_2H_5)_4$, or complexes, such as $Na_2SiF_6$, the silica prepared by the extraction and activation of crystallized natural or synthetic compounds, such as aluminum silicates, aluminosilicates, clays, etc. It is also possible to use hydrolyzable tetravalent silicon compounds, such as the silicon halides.

Among the sources of titanium oxide, representative are crystallized or amorphous titanium oxides or hydroxides, tetravalent titanium compounds that may be hydrolyzed, such as halides ($TiCl_4$), alcoholates, soluble titanium salts, such as $TiOSO_4$, $(NH_4)_2 TiO(C_2O_4)_2$, etc.

It is also possible to use as sources of silica or titanium oxide compounds containing the elements Si and Ti, such as, for example, glasses or gels based on the oxides of these two elements.

The sources of silica and titanium oxide may be employed in the soluble form or as solid powders, but also in the form of agglomerates, such as, for example, extruded tablets capable of being converted to a zeolite of the desired structure without modifying their form.

The fluoride anions may be introduced in the form of hydrofluoric acid, salts thereof, such as, for example, NH$_4$F, NH$_4$HF$_2$, NH(C$_3$H$_7$)$_3$F, N(C$_3$H$_7$)$_4$F, hydrolyzable compounds releasing fluoride anions in the reaction medium, such as, for example, SiF$_4$, (NH$_4$)$_2$SiF$_6$, (NH$_4$)$_2$TiF$_6$ or similar compounds.

Ammonium fluoride or acid ammonium fluoride are the preferred salts. These salts are highly soluble and introduce no undesirable elements, for, furthermore, they are readily eliminated upon completion of the crystallization.

Suitable structuring agents according to the invention are:

(i) Amines of the Formula I:

wherein R$_1$, R$_2$ and R$_3$, which may be identical or different, are each an alkyl group, preferably a propyl or butyl group;

(ii) Quaternary ammonium compounds of the Formula II:

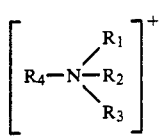

wherein R$_1$, R$_2$, R$_3$ and R$_4$, which may be identical or different, are each alkyl groups, preferably propyl or butyl groups; and (iii) Compounds of the Formulae I and II, in which the nitrogen has been replaced by a phosphorus atom.

In a preferred embodiment of the invention, the structuring agents are tripropylamine or compounds adapted to yield tetrapropylammonium cations.

Advantageously, the structuring agent is added to the reaction mixture in the form of an amine salt, or a quaternary ammonium salt providing the aforementioned cations.

In another embodiment of the invention, the reaction mixture may contain a co-mobilizing agent of tetravalent titanium in a molar ratio, relative to the silicon, of from 3 to 0.01 and preferably from 2 to 0.04.

Exemplary co-mobilizing agents suitable for use according to the invention are, for example, oxalic acid and its salts, acetylacetone, tartaric acid and its salts, etc.

The crystallization of the zeolite may be carried out by heating the reaction mixture to a temperature of from approximately 50° C. to 240° C., preferably from 75° C. to 225° C. for the time necessary for crystallization, according to conventional technique in the zeolite art. By way of example, the duration of the heating may range from about 6 to 500 hr.

Heating and crystallization are preferably carried out in a vessel or autoclave internally coated with a layer of, for example, polytetrafluoroethylene.

The reaction mixture may or may not be agitated.

After crystallization, the resulting precipitate is collected, for example by filtration.

The precipitate is then heated, after optimal drying, to a temperature higher than 450° C., preferably higher than 500° C., in order to decompose by calcination or thermal decomposition the organic species contained in the precipitate, such as, for example, the structuring agent, the compensating cations (NH$_4$+).

The titanozeosilites of the invention are selective adsorbents.

Another important characteristic of these compounds is that they have catalytic properties which make it possible for them to be used as catalysts or catalyst supports for conversion reactions of various organic compounds, such as, for example:

The alkylation of hydrocarbons, such as benzene and toluene, the isomerization of paraffins and naphthenes, the conversion of ethers or alcohols into hydrocarbons, oxidation, the dismutation of aromatic compounds such as toluene, reforming, cracking and hydrocracking, the polymerization of acetylenic compounds, the hydrogenation and dehydrogenation of hydrocarbons, the dehydration of aliphatic compounds, the conversion of aliphatic carbonyl compounds or olefins, methanation, and the like.

This invention also features a crystalline product of the type of a zeolite having a MFI structure, based on silica and titanium oxide, that may be obtained by a process comprising:

(i) preparing a reaction mixture in an aqueous medium containing at least one source of silica, a source of titanium oxide, fluoride ions and a structuring agent, the pH of the reaction mixture ranging from about 1.5 to 10.5; and (ii) crystallizing the reaction mixture and recovering the resulting crystalline precipitate.

The molar ratios of the different constituents of the reaction medium are those indicated above.

The crystalline precipitate is advantageously washed to eliminate impurities therefrom and in particular cations or anions not attached to or incorporated in the final structure.

Such material is particularly and principally used for the production of MFI zeolites by calcination under appropriate conditions, determined as a function of the desired final application of the zeolite.

In order to further illustrate the present invention and the advantages thereof, the following specific examples are given, it being understood that same are intended only as illustrative and in nowise limitative.

EXAMPLE 1

13.8 g of anastase type TiO$_2$ were dissolved in 51.8 g of a 50% aqueous solution of HF. To this solution, 12.5 g Aerosil silica (SiO$_2$) were added. After mixing, a second solution, obtained by dissolving 27.8 g tetrapropylammonium bromide (TPABr) in 44.5 g water, was added and the mixture agitated. Subsequently, always under agitation, an aqueous solution of 25% ammonia was added until the pH ranged from 6 to 6.5. In this manner, a homogeneous gel was produced, to which 0.25 g of a zeolite having a MFI structure were added as crystallization nuclei.

The molar ratios in the reaction mixture were: Ti/Si=0.83; F/Si=6.2; TPA+/Si=0.5; NH$_4$+/Si=3.3; H$_2$O/Si=28.

The reaction mixture was transferred to an autoclave lined with polytetrafluoroethylene and heated for 2 days at 170° C.

After filtering, washing with hot water and drying, 8.5 g of pure, MFI type zeolite, or titanozeosilite identified by X-ray diffraction of the calcined product, were obtained. The measured values of $d_{hkl}$ and $I/I_o$ were in agreement with the values in Table I.

The size of the crystals ranged from 0.5 to 5 μm. After calcination at 550° C. for 4 hr, chemical analysis of the final product evidenced a Si/Ti ratio of 26 and a F content of 0.14%.

EXAMPLE 2

12.5 g Si(OC$_2$H$_5$)$_4$ and then 5.10 g Ti(OC$_4$H$_9$)$_4$ were slowly poured under strong agitation into a solution containing 32.4 g water, 4 g TPA-Br and 1.1 g NH$_4$F. 0.072 g crystals having a MFI structure were added as the nuclei. The pH was 7.5.

The molar composition of the gel obtained in this manner was characterized by the following molar ratios:

Ti/Si=0.25;   F/Si=0.5;   TPA+/Si=0.25;   NH$_4$+/Si=0.5; H$_2$O/Si=30.

This gel was heated in an autoclave lined with polytetrafluoroethylene (PTFE) for 6 days at 200° C. The pH of the medium upon opening the autoclave was 8.5. After separation and washing with hot water, 4.9 g of solids were obtained, the radiocrystallographic analysis of which indicated that it consisted essentially of a MFI type zeolite, with a crystallized impurity of the anastase type. Polarizing microscope examination showed also the presence of amorphous material.

EXAMPLE 3

A mixed gel containing the elements Si and Ti were prepared by admixing 0.1 mole Si(OC$_2$H$_5$)$_4$ and 0.00125 mole Ti(OC$_4$H$_9$)$_4$, to which 2 g acetonylacetone, 2 g n-butanol and 150 g water were added. The mixture, heated under reflux for 3 hr, was converted into a colloidal suspension which was then evaporated and dried at 80° C. 6.2 g of a mixed gel (SiO$_2$, TiO$_2$) having a molar ratio of Si/Ti=80, were produced in this manner.

1.85 g of this mixed were dispersed with 0.040 g MFI type zeolite (nuclei) in an aqueous solution containing 0.64 g TPA-Br, 0.11 g NH4F and 16.2 g water. The reaction mixture which had the following composition, relative to 1 mole SiO$_2$: 1 SiO$_2$; 0.0125 TiO$_2$; 0.08 TPA-Br; 0.1 NH$_4$F; 30 H$_2$O, was heated for 4 days at 200° C. The crystallized solids were separated by filtration, washed and dried and the calcined for 6 hr at 550° C.

Radiocrystallographic analysis indicated that it was a MFI type pure zeolite with an X-ray diffraction pattern consistent with that of Table I. Chemical analysis showed a molar ratio Si/Ti=95.

EXAMPLE 4

Four identical reaction mixtures were prepared according to the following procedure:

2.72 g Ti(OC$_4$H$_9$)$_4$ were hydrolyzed in 20 ml water by agitating the mixture for 6 hr. The resulting precipitate was filtered, then dissolved hot in 20 ml water in the presence of 2.02 g oxalic acid (C$_2$H$_2$O$_4$). To this solution of titanium oxalate, a solution containing 5.33 g tetrapropylammonium bromide (TPA-Br), 1.48 g ammonium fluoride (NH$_4$F) and 23.2 g water, was added. After mixing, 4.8 g silica of the Aerosil 130 type were dispersed in the solution. The molar composition, relative to 1 mole silica of the reaction, was as follows:

1 SiO$_2$; 0.1 TiO$_2$; 0.2 C$_2$H$_2$O$_4$; 0.25 TPA-Br; 0.5 NH$_4$F; 30 H$_2$O.

The four reaction mixtures were then crystallized at 200° C. in autoclaves lined with PTFE, according to the procedures reported in Table II.

TABLE II

| | Operating Conditions | | | |
|---|---|---|---|---|
| Example | Nuclei (1) | Agitation | Duration | Phases Obtained |
| 4a | 0% | none | 2 days | 35% MFI type zeolite + 65% amorphous + impurities |
| 4b | 2% | none | 1 day | 75% MFI type zeolite + 25% amorphous + impurities |
| 4c | 2% | none | 2 days | >90% MFI type zeolite |
| 4d | 2% | yes | 1 day | >90% MFI type zeolite |

(1) The nuclei consisted of MFI type zeolite

The amount added is indicated in % by weight relative to the weight of the silica used.

After crystallization, the solid phases were separated by filtration, washed with water and dried at 40° C. After calcination at 550° C. for 4 hr, the solid phases were identified by their X-ray diffraction spectra. It was determined that the formation of the MFI type zeolites (titanozeosilite) was more rapid in the presence of seed nuclei and in an agitated medium. Chemical analysis of the product of Example 4c indicated an overall Si/Ti molar ratio of 25. The molar ratio Si/Ti in the skeleton of the zeolite was estimated from the measurement of the relative distances of the diffraction peaks. A value of approximately 50 was found.

The X-ray diffraction spectrum of the zeolite obtained in Example 4c is reported in Table IV.

EXAMPLE 5

The 7 experiments of Example 5 indicate that the crystallization of the zeolite of MFI type (titanozeosilite) and the incorporation of the element Ti in the skeleton of the zeolite may be controlled by varying the quantities of the mobilizer (F$^-$) and Ti specific co-mobilizer (oxalic acid). These experiments were carried out using reaction mixtures similar to those used in Example 4. In experiments 5b to 5f, the use of lesser amounts of oxalic acid, together with the absence of oxalic acid in Experiment 5g, resulted in the incomplete dissolution of the resulting precipitate, after hydrolysis of the Ti(OC$_4$H$_9$)$_4$. All contained 2% crystallizing nuclei. The molar compositions relative to 1 mole of silica and the pH are reported in Table III.

TABLE III

| Example | SiO$_2$ | TiO$_2$ | TPA-Br | NH$_4$F | C$_2$H$_2$O$_4$ | H$_2$O | pH, initial | pH, final | Si/Ti estimated |
|---|---|---|---|---|---|---|---|---|---|
| 5a | 1 | 0.1 | 0.08 | 0.5 | 0.2 | 30 | 4 | 7 | 75 |
| 5b | 1 | 0.1 | 0.08 | 0.5 | 0.1 | 30 | 5 | 6 | 35 |
| 5c | 1 | 0.1 | 0.08 | 0.25 | 0.05 | 30 | 6 | 6 | 50 |
| 5d | 1 | 0.1 | 0.08 | 0.1 | 0.1 | 30 | 3 | 5 | 45 |
| 5e | 1 | 0.1 | 0.08 | 0.1 | 0.05 | 30 | 4 | 5.5 | 80 |
| 5f | 1 | 0.1 | 0.08 | 0 | 0.05 | 30 | 1.5 | 3.5 | amorphous |
| 5g | 1 | 0.1 | 0.08 | 0 | 0 | 30 | 6 | 6 | amorphous |

The 7 reaction mixtures were heated for 4 days at 200° C. in non-agitated autoclaves lined internally with PTFE. After filtration, washing and drying, the solids were calcined for 4 hr in an open crucible.

Radiocrystallographic examination of the 7 samples showed that, with the exception of the products 5f to 5g, MFI type zeolites (titanozeosilite) were produced, which were well crystallized and may contain certain impurities.

The Si/Ti ratio (last column of Table III) was estimated from the measurement of the relative distances of the diffraction peaks.

Several conclusions may be drawn from examination of these results. On the one hand, the presence of the mobilizer ($F^-$) was necessary to effect crystallization. On the other, the Si/Ti ratio may be modified by varying the quantities of the mobilizer ($F^-$) and the co-mobilizer $(COOH)_2$. Excessive or insufficient amounts of the latter two components were less favorable as regards incorporation of the element Ti in the skeleton of the zeolite.

EXAMPLE 6

This example illustrates the use of acetylacetone as a specific co-mobilizer in place of oxalic acid.

0.8 g acetylacetone was mixed with 1.36 g Ti-$(OC_4H_9)_4$ and, under strong agitation, a solution containing 0.37 g $NH_4F$ and 0.85 g TPA-Br in 36 g $H_2O$, then 2.40 g Aerosil silica and 0.040 g nuclei (MFI type zeolite) were added. The molar composition relative to 1 mole of silica then was: 1 $SiO_2$; 0.1 $TiO_2$; 0.08 TPA-Br; 0.25 $NH_4F$; 0.2 acetylacetone; 50 $H_2O$.

The crystallization of the reaction mixture was carried out under the same conditions as in Example 5. After separation and calcination, a crystallized solid was obtained; its X-ray diffraction pattern was in agreement with that of Table I. The Si/Ti ratio in the skeleton was estimated by measuring the relative displacement of the diffraction peaks at approximately 45.

COMPARATIVE EXAMPLE 7

As a comparison, a porous synthetic material was prepared according to the process described in published French Application No. 2,471,950 and is designated TSI therein.

The process uses a basic solution with $OH^-$ ions as the mobilizing agent.

227.5 g tetraethylorthosilicate were placed in a Pyrex glass vessel equipped with an agitator and maintained under an atmosphere free of $CO_2$ and 7.5 g tetraethyltitanate were added, followed by the progressive addition of 500 g of a solution of 20% by weight tetrapropylammonium hydroxide.

The mixture was maintained under agitation for approximately 1 hr prior to heating to accelerate the hydrolysis and the evaporation of the ethyl alcohol.

After 5 hr of heating at 80°-90° C., water was added. The homogeneous, opalescent solution was transferred to a stainless steel autoclave equipped with an agitator. The mixture was heated to 165° C. and maintained under agitation at this temperature under its own pressure for 10 days. The autoclave was then cooled and the resulting mass of fine crystals was recovered. After washing the crystals with water, they were dried, then calcined for 6 hr at 550° C.

The X-ray diffraction spectrum obtained for the calcined produced corresponded to that indicated in Table I of said French Application No. 2,471,950.

In Table IV, the X-ray diffraction spectra of the zeolite according to the invention and obtained in Example 4c, and those of the product of Comparative Example 7, are reported.

The differences in the spectra of the two products are obvious and clearly evidence that the zeolite obtained with fluoride ions as the mobilizing agent contains titanium in its skeleton. This difference was confirmed by the crystalline system obtained, which is monoclinic for a zeolite of the invention and orthorhombic for a titanium silicate obtained in a basic medium.

TABLE IV

Comparison of the X-ray diffraction diagrams corresponding to a titanozeosilite (Example 4c) and a titanium silicalite according to Comparative Example 7

| Titanozeosilite (Example 4c) | | Titanium silicalite (Example 7) | | Titanozeosilite (Example 4c) | | Titanium silicalite (Example 7) | |
|---|---|---|---|---|---|---|---|
| $d_{hkl}$ (nm) | $I/I_o$ | $d_{hkl}$ (nm) | $I/I_o$ | $d_{hkl}$ (nm) | $I/I_o$ | $d_{hkl}$ (nm) | $I/I_o$ |
| 1.12 | F-FF | 1.114 | FF | 0.462 | f | | |
| 1.00 | F-FF | 0.999 | F | 0.446 | ff | | |
| 0.98 | f | 0.974 | m | 0.436 | f | 0.4360 | f |
| 0.90 | ff | | | 0.426 | ff | 0.4260 | mf |
| 0.805 | ff | | | 0.4084 | ff | | |
| 0.746 | ff | | | 0.4008 | f | | |
| 0.709 | ff | | | 0.3859 | F | 0.3855 | F |
| 0.671 | F | 0.6702 | f | 0.3826 | mF | 0.3819 | F |
| 0.637 | f | 0.6362 | mf | 0.3806 | mF | | |
| 0.600 | fm | 0.5993 | mf | 0.3759 | m | 0.3751 | F |
| 0.594 | f | | | 0.3742 | m | | |
| 0.573 | f (m) | 0.5698 | f | 0.3718 | m | 0.3720 | F |
| 0.570 | (shoulder) | | | 0.3663 | f | 0.3646 | m |
| 0.559 | f | 0.5574 | f | 0.3627 | f | | |
| 0.538 | f (f) | 0.3448 | f (f) | 0.3444 | f | | |
| 0.534 | f (f) | | | 0.3431 | f | | |
| 0.513 | ff | | | 0.3396 | ff | | |
| 0.504 | ff | 0.5025 | f | 0.3357 | f (f) | | |
| 0.498 | mf | 0.4980 | f | 0.3317 | f | 0.3318 | f |
| 0.488 | ff | | | 0.3256 | f | | |
| 0.471 | ff | | | | | | |

EXAMPLE 8

The zeolite of the invention may be used as an adsorbent, a catalyst and/or a catalyst support in numerous applications.

As one example, its use was tested as a reaction catalyst in the selective dehydration of methylbutanol to methylbutene.

30 g of the catalyst prepared according to Example 1 were added to 300 ml of 0.1N hydrochloric acid. This mixture was heated to 60° C. and maintained at this temperature under agitation for 4 hr.

The catalyst was recovered by filtration and washed with water. After drying in an oven at 100.C, the catalyst was ground.

The catalyst was placed in a column between two beds of glass beads and maintained at 500° C. overnight for activation.

The methylbutanol was fed continuously into the column under a nitrogen atmosphere, at a temperature of 280° C. and with a gas flow of 16 l/hr.

The product recovered was analyzed by gas phase chromatography.

The percentage of methylbutene in the output mixture was approximately 85% for a reaction time of about 2 hr.

Using a conventional catalyst based on gamma-alumina, this proportion was approximately 65%.

These results evidence that the catalyst of the invention has better selectivity.

However, the yield of the conversion of methylbutanol is lower for the catalyst of the invention relative to alumina base catalyst.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims including equivalents thereof.

What is claimed is:

1. A calcined MFI zeolite having the formula:

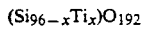

wherein x ranges from about 0.1 to 6, said MFI zeolite having a monoclinic crystalline network.

2. The MFI zeolite as defined by claim 1, having the X-ray diffraction pattern set forth in Table I.

3. The MFI zeolite as defined by claim 1, comprising from 0.01 to 0.8% by weight of fluorine.

4. The MFI zeolite as defined by claim 1, devoid of fluorine values.

5. A process for the preparation of the MFI zeolite as defined by claim 1, comprising (i) formulating an aqueous reaction medium having a pH ranging from 1.5 to 10.5 and which comprises at least one source of silicon oxide, at least one source of titanium oxide, fluoride ions, and a structuring agent, the Ti/Si molar ratio therein ranging from 0.002 to 1.5, the F/Si molar ratio therein ranging from 0.04 to 10, the H$_2$O/Si molar ratio therein ranging from 4 to 400, and the structuring agent/Si molar ratio therein ranging from 0.02 to 2; (ii) crystallizing such reaction mixture; and (iii) recovering and calcining the resulting crystalline precipitate at a temperature greater than about 450° C.

6. The process as defined by claim 5, said Ti/Si molar ratio ranging from 0.01 to 1.

7. The process as defined by claim 6, said F/Si molar ratio ranging from 0.06 to 6.

8. The process as defined by claim 7, said H$_2$O/Si molar ratio ranging from 6 to 100.

9. The process as defined by claim 8, said structuring agent/Si molar ratio ranging from 0.04 to 1.

10. The process as defined by claim 5, said reaction medium including a common source of the silicon oxide and titanium oxide.

11. The process as defined by claim 5, said structuring agent comprising a tertiary amine having the formula I:

wherein R$_1$, R$_2$ and R$_3$, which may be identical or different, are each an alkyl group.

12. The process as defined by claim 11, wherein the formula I, R$_1$, R$_2$ and R$_3$ are propyl or butyl.

13. The process as defined by claim 5, said structuring agent comprising a quaternary ammonium salt having the formula II:

wherein R$_1$, R$_2$, R$_3$ and R$_4$, which may be identical or different, are each an alkyl group.

14. The process as defined by claim 13, wherein the formula II, R$_1$, R$_2$, R$_3$ and R$_4$ are propyl or butyl.

15. The process as defined by claim 5, said structuring agent comprising a compound having the formula:

wherein R$_1$, R$_2$ and R$_3$, which may be identical or different, are each an alkyl group.

16. The process as defined by claim 5, said structuring agent comprising a compound having the formula:

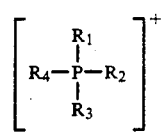

wherein R$_1$, R$_2$, R$_3$ and R$_4$, which may be identical or different, are each an alkyl group.

17. The process as defined by claim 5, said at least one source of silicon oxide comprising a hydrogel, aerogel, colloidal silica suspension, silicic ester, water soluble silicate, silica derived from a natural or synthetic crystalline compound, or hydrolyzable tetravalent silicon compound.

18. The process as defined by claim 17, said at least one source of titanium oxide comprising a natural or synthetic titanium oxide or hydroxide, halide, alcoholate, or water soluble titanate salt.

19. The process as defined by claim 5, said reaction mixture comprising at least one titanium co-mobilizing agent, in a molar ratio relative to silicon, of from 0.01 to 3.

20. The process as defined by claim 19, said co-mobilizing agent comprising oxalic acid or salt thereof, acetylacetone, or tartaric acid or salt thereof.

21. The process as defined by claim 5, the fluoride ions in said reaction mixture being derived from hydrofluoric acid, ammonium or amine fluoride, or a hydrolyzable compound releasing fluoride anions.

22. The process as defined by claim 21, said fluoride ions being derived from titanium fluoride, silicon fluoride, a double ammonium and titanium fluoride, or a double ammonium and silicon fluoride.

23. The process as defined by claim 5, said reaction mixture having a pH of from 5 to 10.5; a molar ratio of Ti/Si ranging from 1.5 to 0.002; a molar ratio of F/Si ranging from 10 to 0.04; a molar ratio of $H_2O$/Si ranging from to 4; and a molar ratio of structuring agent/Si ranging from 2 to 0.02.

24. A selective adsorbent comprising the MFI zeolite as defined by claim 1.

25. A catalyst comprising the MFI zeolite as defined by claim 1.

26. A catalyst support comprising the MFI zeolite as defined by claim 1.

* * * * *